United States Patent [19]

Berry

[11] Patent Number: 4,965,110

[45] Date of Patent: Oct. 23, 1990

[54] ELECTROSTATICALLY PRODUCED STRUCTURES AND METHODS OF MANUFACTURING

[75] Inventor: John P. Berry, Wirral, England

[73] Assignees: Ethicon, Inc.; The University of Liverpool, both of Somerville, N.J.

[21] Appl. No.: 368,015

[22] Filed: Jun. 19, 1989

Related U.S. Application Data

[60] Continuation-in-part of Ser. No. 208,946, Jun. 20, 1988, abandoned, which is a division of Ser. No. 896,789, Aug. 15, 1986, abandoned.

[51] Int. Cl.$^5$ .................................................. A61F 2/06
[52] U.S. Cl. .................................. 428/36.4; 428/36.3; 428/212; 428/220; 428/286; 428/297; 428/298; 428/303; 428/311.1; 428/903; 623/1
[58] Field of Search ...................... 428/36.3, 36.4, 297, 428/298, 286, 903, 303, 220, 212, 311.1; 623/1

[56] References Cited

U.S. PATENT DOCUMENTS

| 4,044,404 | 8/1977 | Martin et al. | 3/19 |
| 4,143,196 | 3/1979 | Simm et al. | 428/212 |
| 4,323,525 | 4/1982 | Bornak | 264/24 |
| 4,331,730 | 5/1982 | Sorenson | 428/286 |
| 4,345,414 | 8/1982 | Bornat et al. | 53/425 |
| 4,475,972 | 10/1984 | Wong | 156/167 |
| 4,657,793 | 4/1987 | Fisher | 428/36.3 |
| 4,689,186 | 8/1987 | Bornat | 264/6 |
| 4,725,273 | 2/1988 | Kira | 623/1 |
| 4,743,250 | 5/1988 | Kitagawa et al. | 623/1 |
| 4,743,252 | 5/1988 | Martin, Jr. et al. | 623/1 |

FOREIGN PATENT DOCUMENTS

| 1530990 | 11/1978 | United Kingdom . |
| 2120946 | 12/1983 | United Kingdom . |
| 2121286 | 12/1983 | United Kingdom . |
| 2142870 | 1/1985 | United Kingdom . |
| 2181207 | 4/1987 | United Kingdom . |

Primary Examiner—Ellis P. Robinson
Assistant Examiner—Archene A. Turner
Attorney, Agent, or Firm—Robert L. Minier

[57] ABSTRACT

A tubular fibrous structure having smaller diameter fibers randomly oriented and larger diameter fibers and/or bundles of fibers circumferentially oriented. The structure includes elongated voids also generally circumferentially oriented.

10 Claims, 7 Drawing Sheets

SEM of the microstructure of a composite graft.
Scale: 1mm. = 1μm.

ELFR Response at 15% extension.

| Extension | $C_{stat}$ |
|---|---|
| 15% | 0.66% |
| 20% | 0.73% |
| 25% | 0.79% |

Photograph of a composite graft undergoing a bend test.

FIG-7  RESULTS OF BENDING EXPERIMENTS

| TUBE CODE NUMBER | TYPE | INT DIA mm | EXT DIA mm | WALL mm | ATMOSPHERIC PRESSURE BEND DIA mm | BEND DIA OD | 80 mm Hg BEND DIA mm | BEND DIA OD | 200 mm Hg % EXTENSION |
|---|---|---|---|---|---|---|---|---|---|
| NQd (X) | STANDARD CAROT ID | 3.67 | 4.55 | 0.44 | 79.9 | 17.8 | 53 | 11.6 | 4* |
| NQd (21) | " | 3.67 | 4.53 | 0.43 | 85.4 | 18.9 | 54 | 11.9 | 4* |
| NQd (22) | " | 3.46 | 4.28 | 0.41 | 75.5 | 17.7 | 55 | 12.8 | 4* |
| ELF 29 | NEW DESIGN | 4.56 | 5.3 | 0.37 | 10.4 | 1.96 | 8 | 1.5 | 15 |
| ELF 31 | " | 3.54 | 4.4 | 0.43 | 15.2 | 3.45 | 13 | 2.9 | ** |

\* RESULTS FROM MEASUREMENTS DONE ON SIMILAR GRAFTS

\*\* NOT MEASURED

ELECTROSTATICALLY PRODUCED STRUCTURES AND METHODS OF MANUFACTURING

This is a continuation-in-part patent application of copending patent application Ser. No. 208,946 filed June 20, 1988 which is a division of application Ser. No. 896,789 filed Aug. 15, 1986, now abandoned.

BACKGROUND OF THE INVENTION

The invention relates to electrostatically produced structures, for example, tubular vascular grafts, and to methods of manufacturing such structures.

It has been proposed in the past to spin electrostatically fibrous structures of polymeric material such as polyurethane using an electrostatically charged, spinning mandrel as a fiber collector, a solution of the polymer being ejected towards the mandrel from a manifold of capillary needles or other suitable means. The mandrel may be replaced by an alternative electrostatically charged collector if a tubular structure is not required.

It has been found that synthetic fibrous structures built up in this way generally have fibers of a diameter not larger than 1 $\mu$m and that the fibers are generally randomly oriented. Some directional bias can be induced by varying the speed of mandrel rotation, as indicated in our published British Patent application Nos. 2121286A and 2120946A.

It has been found that the generally random nature of the fibrous structure and the small fiber size of 1 $\mu$m or less has produced a tubular structure which can be prone to kinking and can therefore be a problem when used as an arterial graft particularly where limb movement is involved.

In the past, attempts have been made to control the orientation of the fibers as they are deposited on the mandrel. For example, in U.S. Pat. No. 4,689,186 the mandrel is placed between charged electrodes or grids in order to control fiber orientation. As shown and described in U.S. Pat. No. 4,689,186 droplets of fiberizable solution are forced to form on the tips of the manifold needles and are electrostatically drawn towards the charged mandrel. Each droplet is elongated into a thin stream which dries out to form a solid fiber. The path traced by a fiber on its journey towards the mandrel is helical. The radius of the helix is maximum approximately half way between the needles and the mandrel and is minimum at each end of the path. Each needle produces a single fiber, but because the velocity of the fiber is high (30 m/s) and the path is helical, it gives an optical illusion of appearing as a spray or jet, as schematically depicted in FIG. 6(b) of the patent.

While controlling the fiber orientation of a tubular structure can improve many of the physical properties of the structure, it does not eliminate the kinking problem and does not produce a vascular graft that is acceptable for use in all of the desired replacement areas of a natural vessel.

SUMMARY OF THE PRESENT INVENTION

According to one aspect of the invention, there is provided a tubular fibrous structure comprising small diameter fibers and substantially larger diameter fibers, said smaller diameter fibers being randomly oriented in the fibrous structure, said larger diameter fibers being embedded in a matrix of said small diameter fibers and said larger diameter fibers being generally oriented circumferentially with respect to the longitudinal axis of said tubular structure.

The structure may comprise a multiplicity of elongate voids extending generally circumferentially with respect to the longitudinal axis of the structure.

The small diameter fibers may have a diameter in the range 0.5 $\mu$m to 2 $\mu$m for example 1 $\mu$mm and the larger diameter fibers may have a diameter in the range 2 $\mu$m to 15 $\mu$m. The larger the fiber diameter, the more likely the fiber is to be oriented circumferentially In some instances, the larger diameter fibers may be cable-like, being bundles or agglomerations of the smaller diameter fibers.

The structure may comprise an inner layer of fibers of the small diameter. The layer of fibers of larger diameter mixed with smaller diameter fibers may be an intermediate layer, inside an outer layer of fibers of the small diameter.

The inner layer may be of a polymeric material adapted to be compatible with contact with blood, and may be of a thickness in the range 10 $\mu$m to 60 $\mu$m preferably 40 $\mu$m.

The intermediate layer may be of a thickness in the range 300 $\mu$m to 2000 $\mu$m.

The outer layer may be of a thickness in the range of 10 $\mu$m to 60 $\mu$m preferably 40 $\mu$m.

According to a further aspect of the invention, there is provided a tubular fibrous structure comprising small diameter fibers and substantially larger diameter fibers, said small diameter fibers being randomly oriented in the tubular structure, at least a portion of said larger diameter fibers being embedded in a matrix of small diameter fibers, and said larger diameter fibers being generally oriented circumferentially to the longitudinal axis of said tubular structure, said tubular structure having open areas or voids between the larger diameter fibers, said open areas or voids extending in the circumferential direction as the tubular structure whereby said structure has a low modulus in both compression and extension in the axial direction of said tubular structure.

According to a further aspect of the invention, there is provided a method of electrostatically spinning a tubular fibrous structure using an electrostatically charged, spinning mandrel and an electrostatically charged grid means in the region of the mandrel to produce an electrostatic field, which method comprises the steps of introducing into said electrostatic field a fiberizable material, collecting on said mandrel a first portion of said liquid in the form of fibers attached directly to the mandrel and a second portion of said liquid in the form of fibers traveling first to one of the grid means and then to the mandrel to follow a longer path to said mandrel than the fibers from said first portion of liquid, whereby a tubular fibrous structure is produced having fibers of different diameters and varying fiber orientations.

In the preferred embodiment of the present invention, there is provided a method of electrostatically spinning a tubular fibrous structure using an electrostatically charged, spinning mandrel and a pair of electrostatically charged grid means in the region of the mandrel and disposed on opposite sides of the mandrel to produce an electrostatic field, and means for introducing fiberizable material into the electrostatic field, which method comprises the steps of arranging the grid means of such that the electrostatically charged surface of one of the grid means is nearer the mandrel than the other grid means, selecting desired electrostatic potentials for the mandrel and the grid means, and introducing said fiberizable material into the electrostatic field, whereby a tubular fibrous structure is produced having fibers of different diameters and varying fiber orientations. The electrostatic spinning process may be started with the mandrel at a first mandrel voltage and the grid means at a first grid voltage and the mandrel and the grid voltages varied to cause a variation in the diameter and orientation of at least a portion of the fibers forming the tubular fibrous structure.

The first mandrel voltage and the first grid voltage may be such as to produce fibers of a first diameter generally randomly orientated, and the mandrel and grid voltages may be varied by increasing the electrostatic charge on the grid means relative to the mandrel to produce fibers of a larger diameter than the first diameter as well as fibers of the first diameter, the fibers of larger diameter tending to be orientated generally circumferentially with respect to the longitudinal axis of the mandrel.

The method may include a further step of returning the mandrel to the first mandrel voltage and the grid means to the first grid voltage for a period at the end of the process.

The grid means may comprise a pair of coplanar grids or plates each on opposite sides of the mandrel and in a plane parallel to each other.

The mandrel may be charged to a voltage in the range 6 to 20 kV, and an example of a preferred voltage for the mandrel, when of 4 mm diameter, and the grid means is 12 kV for the mandrel, 6 kV for the grid means to produce fibers of the first diameter, 7 kV for the mandrel, 9.2 kV for the grid means when fibers of a larger diameter are to be produced. It will be appreciated, however, that these voltages are quoted merely by way of example as mandrel size, grid spacing and grid location have a fundamental effect on the voltage relationship between the mandrel and the grid means to produce different fiber production on the mandrel.

The tubular fibrous structure may have different fibrous structures at different locations along its length, and this feature may be achieved by traversing the fiberizable material introduction means along the length of the mandrel and varying the electrostatic potentials of the mandrel and the grid means as the fiberizable material introduction means moves relative to the mandrel to produce different electrostatic fields for fiber collection and have different fibrous structures at different axial locations on the mandrel. This variation may be conveniently controlled by a microprocessor programmed to repeat a desired sequence of electrostatic charge variation.

According to a further aspect of the invention, there is provided apparatus for electrostatically spinning a tubular fibrous structure, which apparatus comprises a mandrel to act as a collector for electrostatically spun fibers, means for electrostatically charging the mandrel and for varying the electrostatic charge thereon, means for rotating the mandrel, a pair of grid means disposed on opposite sides of the mandrel, means for electrostatically charging the grid means and for varying the electrostatic charge thereon, and means for introducing a fiberizable material into the electrostatic field, the surface of one of the grid means being closer to the mandrel than the surface of the other grid means.

The apparatus may further comprise microprocessor means for controlling variation of the voltages on the mandrel and the grid means in accordance with a desired sequence to produce a tubular fibrous structure having desired characteristics.

BRIEF DESCRIPTION OF THE DRAWINGS

By way of example, one embodiment of a method of electrostatically spinning a tubular fibrous structure, of apparatus for carrying out the method and of a tubular fibrous structure will now be described with reference to the accompanying drawings, in which:

FIG. 7 is a table of results of bending experiments on a fibrous structure having fibers of different diameter;

FIGS. 1 and 2 illustrate such apparatus diagrammatically. FIG. 1 depicts a general electrostatic spinning process as has been described in several patent specifications already published, for example earlier published British application Nos. 2121286A and 2120946A.

The apparatus consists of an array of capillary needles 10 mounted on a carrier (not shown) with means for moving the carrier in reciprocating fashion parallel to a mandrel 11. The means for moving the needle block is conveniently a motor.

The mandrel 11 in the embodiment illustrated is of 4 mm diameter although it will be appreciated that other diameters may be used. There are means for rotating the mandrel at a variety of different speeds but typically the speed will be of several thousand revolutions per minute, a typical speed being 5000 r.p.m.

The capillary needles 10 are supplied with polymeric material such as polyurethane or other suitable polymeric material in solution (although it is possible to use a suspension) and material emanating from the needles is attracted towards the mandrel 11 by electrostatically charging the mandrel 11 to a potential of several kilovolts with respect to the needles 10. The process results in the production of fibers which collect on the mandrel 11 in a manner which has been described in specifications already published.

Figure 1:
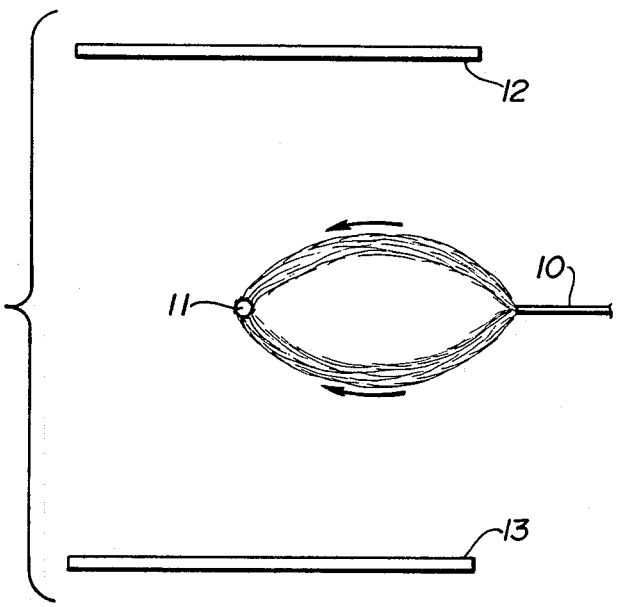
FIG. 1 is a side view of apparatus according to the prior art for spinning a tubular fibrous structure.

It has already been proposed to have electrostatically charged grids on either side of the mandrel 11 with respect to the needles 10 with the edges of the grids nearest the needles 10 significantly nearer the needles than has the mandrel. In the apparatus of FIG. 1 and a pair of plates 12 and 13 are provided. The plates 12 and 13 are conveniently of metallic sheeting although barred grids may be used is desired.

In the mode of operation illustrated in FIG. 1, both plates 12 and 13 are electrostatically charged to a voltage less than the voltage to which the mandrel 11 is charged. Typical voltages for the spacing of the plates and the size of the mandrel are 12 kV on the mandrel and 6 kV on the plates. This results in an array of fibers leading from the needles 10 to the mandrel 11 substantially as shown in FIG. 1 with each fiber following a generally uniform helical path as it moves from the needle to the mandrel.

Figure 2:
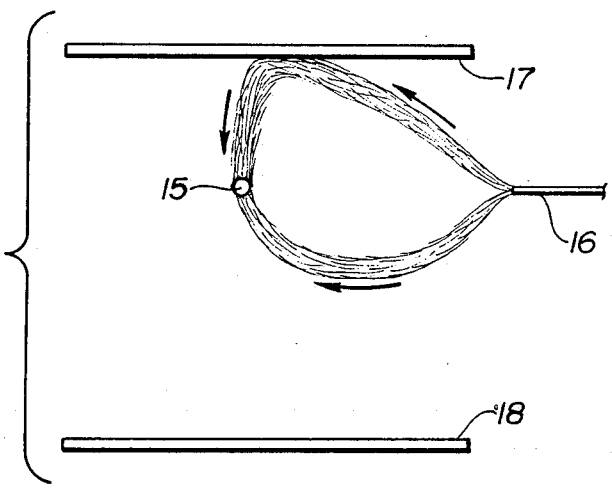
FIG. 2 is a side view of apparatus according to the present invention for spinning a tubular fibrous structure of the invention.

However, by changing the apparatus slightly to that shown in FIG. 2, the fibrous structure formed on the mandrel 15 changes substantially To produce the shape of fiber array emanating from the needles 16 shown in FIG. 2, the electrostatic field is not symmetrical. The top plate 17 is placed closer to the mandrel than is the bottom plate 18. Also, the plates 17 and 18 may be charged to a higher voltage than was the case in FIG. 1 and the mandrel voltage is reduced. This causes fibers to be attracted more readily towards the top plate 17 and thence to the mandrel 11. Some fibers will be attracted directly to the mandrel 11. Fine adjustment of the voltages is required as if the plates 17 and 18 are at too high a potential, material from the needles will simply be attracted to the plates and not necessarily reach the mandrel 11 whereas if the mandrel voltage is too high relative to the plates, the fibrous structure will not differ significantly from that caused by the mode of operation described with reference to FIG. 1.

Typical voltages for the apparatus depicted in FIG. 2 are 9.2 kV on the plates and 7 kV on the mandrel. It will be appreciated, however, that the voltage relationship between the mandrel and the plates will differ depending on the plate size and spacing, the mandrel diameter and the spacing of the needles from the mandrel and the plates.

Figure 3A:
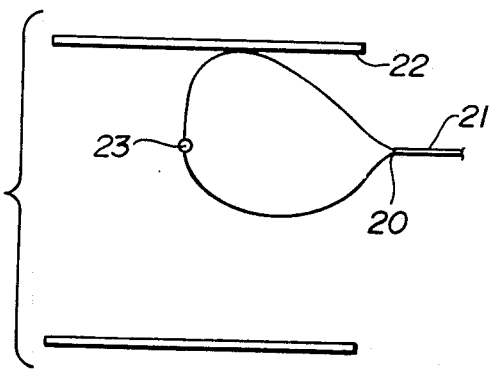
FIGS. 3a, b, and c are idealized schematic drawings depicting different paths that the fiberizable material follows as it is being deposited on the mandrel.
Figure 3B:
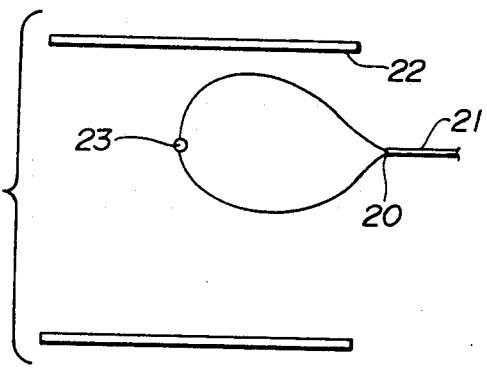
Figure 3C:
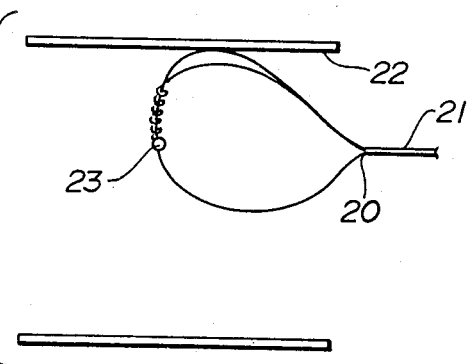
Figure 4:
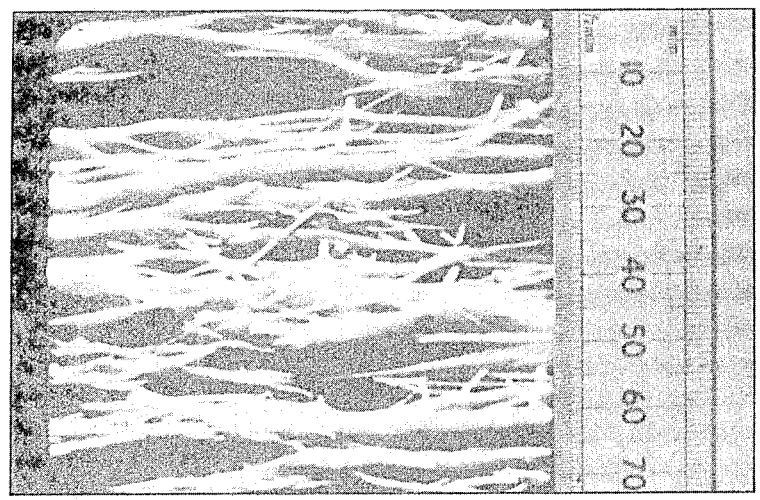
FIG. 4 is a scanning electron microscope photograph of the microstructure of the surface of a tubular structure including fibers of different diameters.

It is believed that the path the fiberizable material takes as it moves from the needle to the mandrel varies as the tubular product is produced. As is diagrammatically shown in FIGS. 3a, 3b and 3c, some of the fiberizable material 20 leaves the needle 21 and moves in an ever increasing helically path until it contacts plate 22 and is then immediately attracted to the mandrel 23 in an almost vertical path as shown in FIG. 3a. Other of the fiberizable material moves directly to the mandrel in a helical path with the diameter of the helix maximum at about the mid point between the needle point and the mandrel as shown in FIG. 3b. Still other of the fiberizable material leaves the needle and moves toward the mandrel in an ever increasing helical path until it contacts fibers passing from the grid to the mandrel where it encircles or agglomerates with such fibers to form a bundle of fibers or a layer diameter fiber which is then attracted to the mandrel as shown in FIG. 3c. The various paths the fiberizable material takes from the needle to the mandrel occurs in a more or less random manner with the fibers taking the shorter paths being of small diameter and generally randomly oriented and the fibers taking the longer paths being of larger diameter or being entangled or forming bundles with adjacent fibers and being generally oriented circumferentially of the resulting structures. As a further result of the various paths the fiberizable material takes and the formation of the larger diameter fibers or bundled and entangled fibers a series of voids are also formed in the resulting tubular structure. Many of these voids are oval or oblong in shape with the larger diameter of the void aligned circumferentially of the resulting structure.

The fibrous structure produced in accordance with the present invention differs significantly from the fibrous structure produced by the mode of operation described with reference to and shown in the prior art in FIG. 1. In the product produced by the apparatus, depicted in FIG. 1, the fibers are generally in the range 0.5 $\mu$m to 2 $\mu$m, and mostly of approximately 1 $\mu$m diameter, and are generally randomly orientated. In the product produced by the apparatus depicted in FIG. 2, however, some fibers have a diameter of approximately 1 $\mu$m (in the range of 0.5 $\mu$m to 2 $\mu$m and their orientation is random, fibers and or bundles of fibers of a larger diameter are also produced. Fibers up to a diameter of 15 $\mu$m may be produced and, in general, the larger the fiber diameter, the more likely that fiber is oriented circumferentially with respect to the longitudinal axis of the mandrel.

Fiber 4 illustrates the type of microstructure of the product of the present invention, it being apparent, that fibers of a diameter of approximately 1 $\mu$m extend randomly in direction over the structure whereas fibers of larger diameter extend generally circumferentially.

Figure 5:
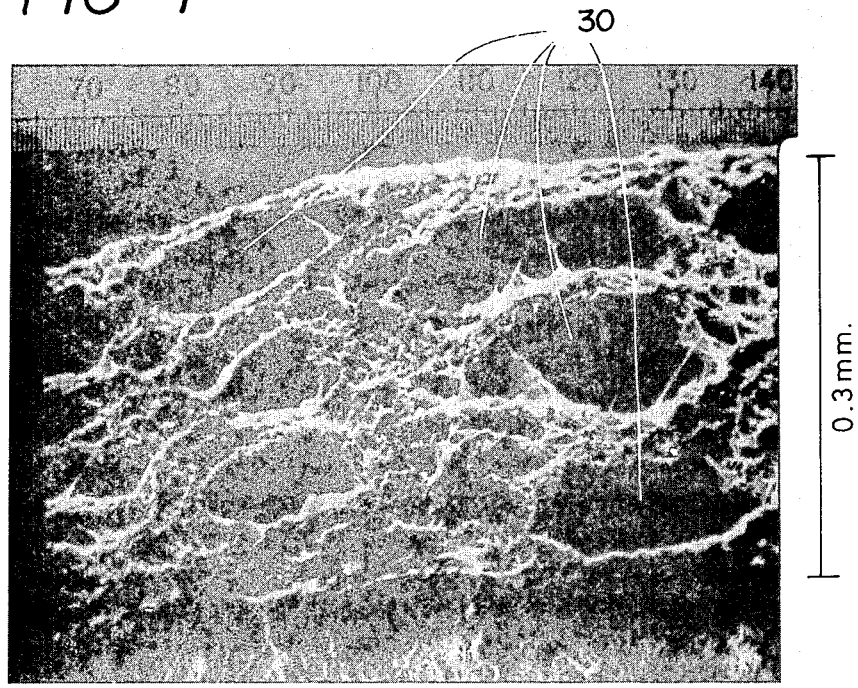
FIG. 5 is a scanning electron microscope photograph of a section through the microstructure of a tubular fibrous structure having fibers of different diameters.

It has also been found that the microstructure produced in accordance with the present invention includes elongate voids in the structure which generally extend circumferentially with respect to the longitudinal axis of the mandrel and the tubular fibrous structure formed on it. FIG. 5 illustrates the presence of the voids 30, FIG. 5 being a scanning electron microscope photograph of a section through the microstructure. The presence of the voids in the microstructure assists in resisting kinking of the structure upon bending.

It will be appreciated that tubular fibrous structures having varying fibrous structures across their cross-section can be produced readily by altering voltages at the mandrel and plates. It is also possible to feed solutions of different polymers to the needles where different material characteristics are required. Thus, a polymer having desirable characteristics for contact with blood and which may also be doped with, for example, a pharmaceutical can be introduced first of all in the FIG. 1 apparatus to build up an inner layer for example of 10 to 60 $\mu$m, preferably 40 $\mu$m for contact with blood. Thereafter, simply by changing the polymer emanating from the needles and the positioning and voltage of the grids and mandrel, the fibrous structure can be altered. Typically, the layer of the structure formed by this technique would be between 300 and 2000 $\mu$m thick. Finally, the apparatus could be converted back to that of the prior art to form an outer layer of perhaps 10 $\mu$m to 60 $\mu$m, preferably 40 $\mu$m of the microstructure including fibers generally of 1 $\mu$m diameter randomly orientated.

Furthermore, it will be appreciated that tubular fibrous structures can be made with different characteristics along the length of the tubular structure by altering voltage or other characteristics as the needles traverse along the mandrel. This can readily be controlled by a microprocessor.

A composite structure as described above including at least a layer of fibers including randomly orientated fibers of approximately 1 $\mu$m diameter together with larger fibers tending to be orientated circumferentially around the tube has the appearance of a lightly ridged, flexible hose. The structure offers little resistance to bending and will assume a very tight loop without kinking. It has greater axial compliance than a similarly dimensioned tubular fibrous structure made entirely by the apparatus depicted in FIG. 1 but, most importantly, when compressed along its axis, it shortens with a minimal tendency to buckle. Mechanical tests have been carried out to quantify these features of the graft.

COMPARISON OF HOOP-AXIAL MODULI

A simplified tensile test was made on specimens cut from a tubular structure made in accordance with the present invention and from a tubular structure made from the apparatus depicted in FIG. 1. The Young's modulus of the "dogbone" shaped specimens was measured and the results are given below:

| hoop modulus | Prior Art | $5.4 \times 10^5$ Pa |
|---|---|---|
| hoop modulus | Present Invention | $20.1 \times 10^5$ Pa |
| axial modulus | Prior Art | $9.7 \times 10^5$ Pa |
| axial modulus | Present Invention | $2.8 \times 10^5$ Pa |

Compared with a prior art structure, the circumferential modulus of the structure of the present invention is increased by a factor of four and the axial modulus is decreased by a similar factor. This shows that the preferential fiber alignment in the structure of the present invention significantly changes the hoop/axial ratio of moduli which explains in part the good bending properties.

The static compliance of the tubular structure of the present invention has been measured using a specimen 7 cm in length, 3.7 mm bore and 0.57 mm wall thickness. The structure was pre-clotted with gelatin prior to being tested and was subjected to 15% axial strain. The internal pressure was ramped to 2000 mm Hg and slowly brought back to zero, during which the change in diameter was repeatedly measured The experiment was repeated at 20% and 25% axial strain.

Figure 6:
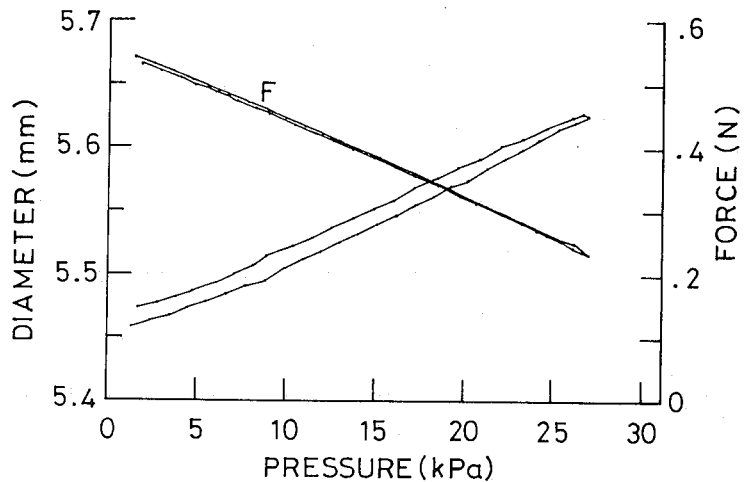
FIG. 6 is a graph of the change in diameter of a tubular structure having fibers of different diameters as a function of internal pressure.

A graph of the change in diameter as a function of internal pressure at 15% axial strain is shown in FIG. 6. The graph is essentially linear with only a small hysteresis. The compliance was calculated by measuring the external diameter at 120 mm Hg and subtracting it from the diameter at 80 mm Hg. This figure was divided by the diameter at 100 mm Hg. The static compliance for each of the three experiments was:

| at 15% extension | 0.66% compliance |
|---|---|
| at 20% extension | 0.73% compliance |
| at 25% extension | 0.79% compliance |

AXIAL EXTENSION UNDER PRESSURE

Owing to the decrease in the axial (longitudinal) Young's modulus of the structure of the present invention, the specimens will elongate when subjected to internal pressure. This extension was measured for a structure of the present invention and for a prior art structure of similar dimensions, the dimensions being

|  | Present Invention | Prior Art |
|---|---|---|
| Int. Diameter | 4.62 mm | 3.74 mm |
| Ext. Diameter | 5.4 mm | 4.46 mm |
| Wall thickness | 0.39 mm | 0.36 mm |

At 200 mm Hg pressure, a structure of the present invention increases in length by 15% compared with less than 4% for a wholly microfibrous, standard prior art structure. A 15% increase is thought to be within clinically acceptable limits.

BENDING CHARACTERISTICS OF THE STRUCTURE OF THE PRESENT INVENTION

The bending characteristics of two typical specimens have been determined at zero and 80 mm Hg internal pressure. The measurements are compared with results from prior art structures of similar dimensions. The term "bending diameter" describes the diameter of the smallest circle around which an unsupported structure will bend without kinking.

Figure 8:
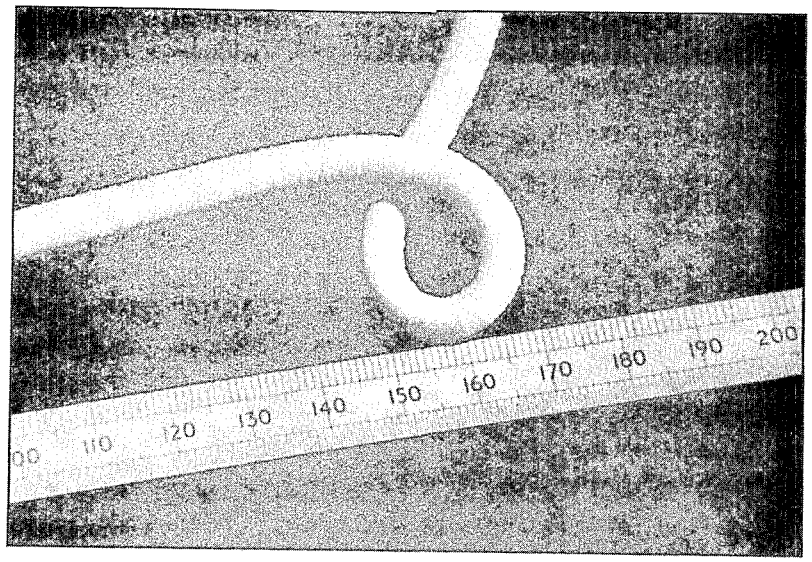
FIG. 8 is a photograph of a fibrous structure having fibers of different diameters undergoing a bend test.

Results of the bending experiments are set out in the table of FIG. 7. The mean bending diameter of a prior art structure is 8 cm. A structure of similar gross dimensions but modified by the inclusion of circumferentially aligned macrofibers in accordance with the present invention is 1.28 cm. FIG. 8 is a photograph of a similar specimen being tested and illustrates the advantageous bending characteristics.

When the specimens are tested under an imposed internal pressure of 80 mm of mercury, the mean bending diameters were 5.4 cm and 1.0 cm respectively.

Figure 9A:
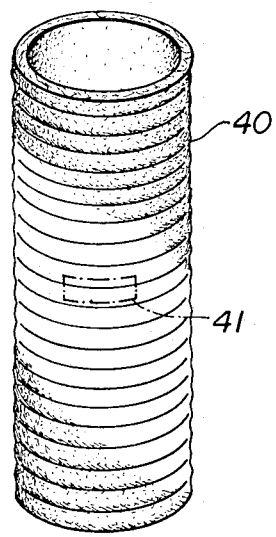
FIG. 9a is a schematic representation of a tubular structure of the present invention depicting the area from which the Scanning Electron Microscope photograph of FIG. 9b was taken.
Figure 9B:
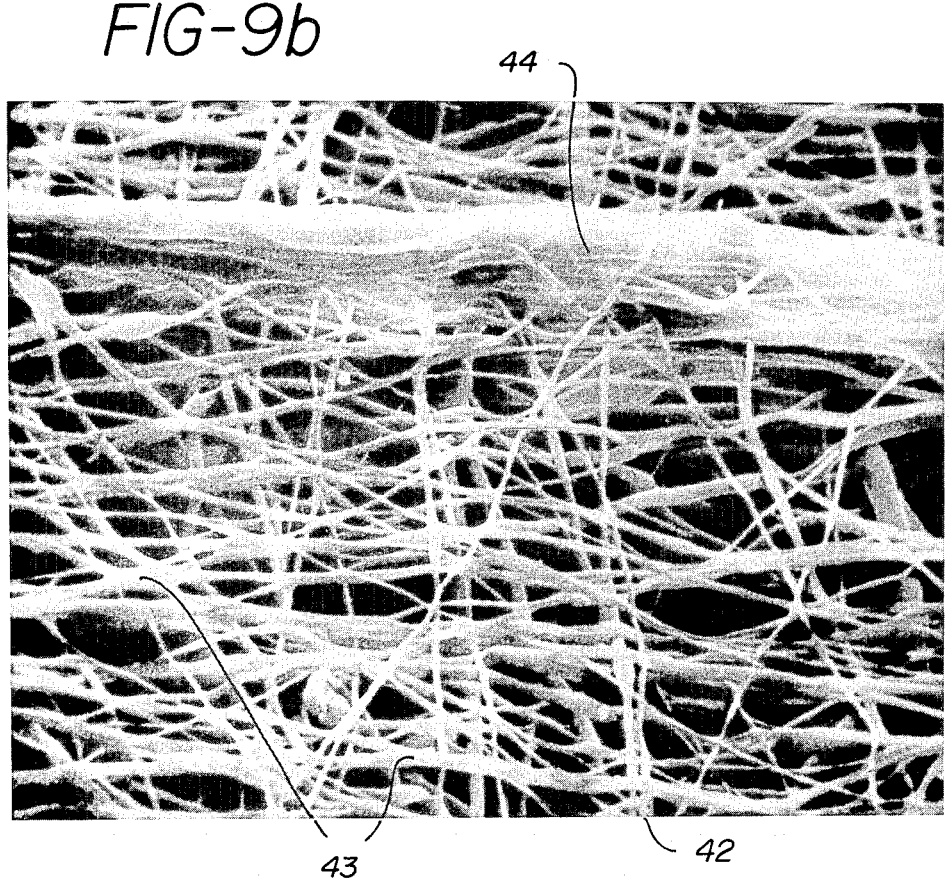

Referring to FIGS. 9a and 9b there is depicted a tubular structure of the present invention. FIG. 9a is a schematic representation of a tubular structure 40. The rectangle 41 denotes the area of the structure from which a Scanning Electron Microscope photograph deposited in FIG. 9b is taken. The photograph is at a magnification of approximately 2000 times. As may be seen there are small diameter fibers 42 randomly oriented. There are also larger diameter fibers 43 generally circumferentially oriented and there is one very large bundle of fibers 44 also circumferentially oriented.

Figure 10A:
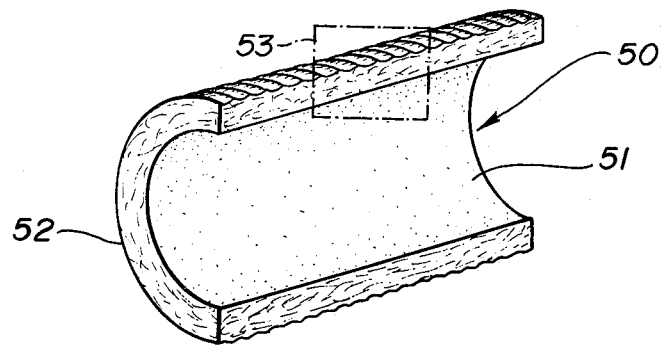
FIG. 10a is a partial cutaway schematic representation of a tubular structure of the present invention depicting the area from which the Scanning Electron Microscope Photograph of FIG. 10b was taken.
Figure 10B:
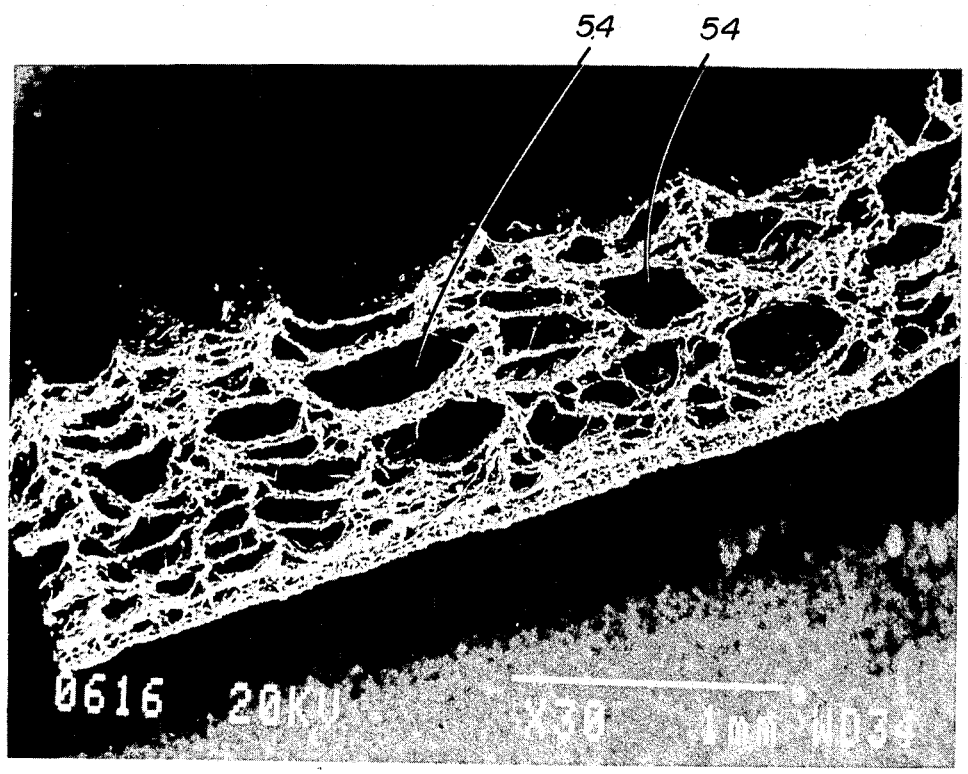

Referring to FIGS. 10a and 10b there is depicted a portion of a tubular structure of the present invention. FIG. 10a is a partial cut away perspective view of the tubular structure 50 showing the inner surface 51 and the outer surface 52. The area 53 denotes the area of the structure from which a cross-sectional Scanning Electron Microscope photograph is taken and shown in FIG. 10b. As shown in FIG. 10b there are a plurality of voids 54 in the tubular structure with the voids generally circumferentially aligned.

It will be appreciated that the apparatus described and the types of structure made can be varied significantly depending on the desired characteristics. It will, of course, be understood that the present invention has been described above purely by way of example and modifications of detail can be made within the scope of the invention.

What is claimed is:

1. A tubular fibrous structure comprising small diameter fibers and substantially larger diameter fibers and bundles of fibers, said smaller diameter fibers being randomly oriented in the fibrous structure, said larger diameter fibers and bundles of fibers being circumferentially oriented with respect to the longitudinal axis of said tubular structure, said structure including a plurality of elongated voids with the larger dimension of such voids being generally oriented circumferentially with respect to the longitudinal axis of said tubular structure.

2. A tubular fibrous structure as claimed in claim 1 wherein the larger diameter fibers are embedded in a matrix of said smaller diameter fibers.

3. A tubular fibrous structure as claimed in claim 1 or claim 2 wherein the smaller diameter fibers have a diameter in the range of 0.5 $\mu$mm to 2 $\mu$mm.

4. A tubular fibrous structure as claimed in claim 1 or 2 wherein the larger diameter fibers and bundles of fibers have a diameter in the range of 2$\mu$ to 15 $\mu$mm.

5. A tubular fibrous structure as claimed in claim 1 or 2 wherein the ratio of the diameters of the larger diameter fibers and bundles of fibers to the diameters of the smaller diameter fibers is less than 30:1.

6. A tubular fibrous structure as claimed in claim 1 or 2 including at least one layer of fibers all of said smaller diameter.

7. A tubular fibrous structure as claimed in claim 6 having a layer of fibers all of said smaller diameter on the inside of the structure.

8. A tubular fibrous structure as claimed in claim 1 or 2 having a layer of fibers of said smaller diameter on the outside of said structure.

9. A tubular structure according to claim 1 or 2 wherein the outer surface of the structure is predominantly larger diameter fibers, bundles of fibers and voids.

10. A tubular structure according to claims 1 or 2 wherein the larger diameter fibers and bundles of fibers form circumferential reinforcing hoops, said hoops being disposed in spaced apart relationship along the length of the graft.

* * * * *